United States Patent [19]
He et al.

[11] Patent Number: 5,922,576
[45] Date of Patent: Jul. 13, 1999

[54] SIMPLIFIED SYSTEM FOR GENERATING RECOMBINANT ADENOVIRUSES

[75] Inventors: Tong-Chuan He, Towson; Bert Vogelstein, Baltimore; Kenneth W. Kinzler, BelAir, all of Md.

[73] Assignee: The John Hopkins University, Baltimore, Md.

[21] Appl. No.: 09/031,917

[22] Filed: Feb. 27, 1998

[51] Int. Cl.$^6$ .............................. C12N 15/64; C12N 1/21; C12N 15/70; C07H 21/04

[52] U.S. Cl. .................. 435/91.41; 435/91.4; 435/252.3; 435/252.33; 435/320.1; 435/471; 435/477; 435/488; 435/455; 536/23.1; 536/23.7; 536/23.72

[58] Field of Search ................................ 435/69.1, 172.1, 435/172.3, 320.1, 252.3, 252.33, 91.4, 91.41, 471, 455, 477, 488; 536/23.1, 23.2, 23.72, 24.1, 23.7

[56] References Cited

PUBLICATIONS

Ballay, et al. "In Vitro and in vitro Synthesis of the Hepatitis B Virus Surface Antigen and of the Antigen and of the Receptor for Polymerized Human Serum Albumin From Recombinant Human Adenoviruses", The EMBO Journal, vol. 4, No. 138, pp. 3861–3885, 1985.

Rosenfeld, et al., "Adenovirus–Mediated Transfer of a Recombinant α 1–Antitrypsin Gene to the Lung Epithelium in Vivo", Science, vol. 252, pp. 431–434, 1991.

Mittal, et al., "Monitoring Foreign Gene Expression by a Human Adenovirus–Based Vector Using the Firefly Luciferase Gene as a Reporter", Virus Research, vol. 28, pp. 67–90, 1993.

Stratford–Perricaudet, et al., "Widespread Long–Term Gene Transfer to Mouse Skeletal Muscles and Heart", Journal of Clinical Investigation, vol. 90, pp. 626–630, 1992.

Graham, et al., "Characteristics of a Human Cell Line Transformed by DNA from Human Adenovirus Type 5", Journal of General Virology, vol. 36, pp. 59–72, 1977.

Ketner, et al., "Efficient Manipulation of the Human Adenovirus Genome as an Infectious Yeast Artificial Chromosome Clone", Proceedings of the National Academy of Sciences, vol. 91, pp. 6186–6190, 1994.

Hardy, et al., "Construction of Adenovirus Vectors Through Cre–loxRecombination", Journal of Virology, Vol. 71, No. 3, pp. 1842–1849, 1997.

Chartier et al., J. Virol., vol. 70, No. 7, pp. 4805–4810, Jul. 1996.

Crouzet et al., PNAS, vol. 94, pp. 1414–1419, Feb. 1997.

*Primary Examiner*—David Guzo
*Attorney, Agent, or Firm*—Banner & Witcoff, Ltd.

[57] ABSTRACT

Recombinant adenoviruses provide a versatile system for gene expression studies and therapeutic applications. This invention describes a strategy which simplifies the generation and production of such viruses. A recombinant adenoviral plasmid is generated with a minimum of enzymatic manipulations, employing homologous recombination in bacteria rather than in eucaryotic cells. Following transfections of such plasmids into a mammalian packaging cell line, viral production can be conveniently followed with the aid of green fluorescent protein, encoded by a gene incorporated into the viral backbone. Homogeneous viruses can be obtained from this procedure without plaque purification. This system expedites the process of generating and testing recombinant adenoviruses.

32 Claims, 5 Drawing Sheets

SIMPLIFIED SYSTEM FOR GENERATING RECOMBINANT ADENOVIRUSES

This invention was made using a U.S. government grant from the NIH CA43460. Therefore, the U.S. government retains certain rights to the invention.

TECHNICAL FIELD OF THE INVENTION

The invention relates to recombinant DNA technology and vectors for gene therapy.

BACKGROUND OF THE INVENTION

Recombinant adenoviruses are currently used for a variety of purposes, including gene transfer in vitro, vaccination in vivo, and gene therapy (1–4). Several features of adenovirus biology have made such viruses the vectors of choice for certain of these applications. For example, adenoviruses transfer genes to a broad spectrum of cell types, and gene transfer is not dependent on active cell division. Additionally, high titers of virus and high levels of transgene expression can generally be obtained.

Decades of study of adenovirus biology have resulted in a detailed picture of the viral life cycle and the functions of the majority of viral proteins (5,6). The genome of the most commonly used human adenovirus (serotype 5) consists of a linear, 36 kb, double-stranded DNA molecule. Both strands are transcribed and nearly all transcripts are heavily spliced. Viral transcription units are conventionally referred to as early (E1, E2, E3 and E4) and late, depending on their temporal expression relative to the onset of viral DNA replication (6). The high density and complexity of the viral transcription units poses problems for recombinant manipulation, which is therefore usually restricted to specific regions, particularly E1, E2A, E3, and E4. In most recombinant vectors, transgenes are introduced in place of E1 or E3, the former supplied exogenously. The E1 deletion renders the viruses defective for replication and incapable of producing infectious viral particles in target cells; the E3 region encodes proteins involved in evading host immunity, and is dispensable for viral production per se.

Two approaches have traditionally been used to generate recombinant adenoviruses. The first involves direct ligation of DNA fragments of the adenoviral genome to restriction endonuclease fragments containing a transgene (7,8). The low efficiency of large fragment ligations and the scarcity of unique restriction sites have made this approach technically challenging. The second and more widely used method involves homologous recombination in mammalian cells capable of complementing defective adenoviruses ("packaging lines") (9,10). Homologous recombination results in a defective adenovirus which can replicate in the packaging line (e.g., 293 or 911 cells) which supplies the missing gene products (e.g., E1) (11). The desired recombinants are identified by screening individual plaques generated in a lawn of packaging cells (12). The low efficiency of homologous recombination, the need for repeated rounds of plaque purification, and the long times required for completion of the viral production process have hampered more widespread use of adenoviral vector technology. Thus there is a need in the art for more efficient techniques for generating recombinant adenoviruses.

SUMMARY OF THE INVENTION

It is an object of the present invention to provide a method for generating recombinant adenoviral vectors containing a gene for expression in mammalian cells.

It is another object of the invention to provide a kit for generating recombinant adenoviral vectors.

It is yet another object of the invention to provide a bacterial cell for generating recombinant adenoviral vectors.

These and other objects of the invention are provided by one or more of the embodiments described below. In one embodiment of the invention, a method for generating a recombinant adenovirus comprising a desired gene is provided. The method comprises the steps of: co-transforming bacteria with: (a) a linear DNA molecule and (b) a supercoiled adenoviral vector, wherein the linear DNA molecule comprises a first segment of DNA comprising one or more desired genes and a second and a third segment of adenoviral genomic DNA, each of said second and thrid segments consisting of at least 500 bp and being sufficient to mediate homologous recombination with the adenoviral vector, wherein the second and third segments flank the first segment, wherein the adenoviral vector comprises a bacterial origin of replication flanked on each side by segments of DNA identical to the second and third segments, whereby subsequent to the step of co-transforming the adenoviral vector and linear DNA molecule recombine to form a recombinant adenoviral vector comprising the desired gene.

In another embodiment of the invention, a kit is provided for generating homologous recombinant adenoviral vectors in bacteria. The kit comprises two plasmids. The first plasmid comprises: a bacterial origin of replication; a first segment of DNA comprising a restriction enzyme site for insertion of a desired gene; a second and a third segment of DNA consisting of adenoviral genomic DNA, each of said second and third segments consisting of at least 500 bp and being sufficient to mediate homologous recombination with an adenoviral vector; wherein the second and third segments flank the first segment. The second plasmid comprises a bacterial origin of replication flanked on each side by DNA segments identical to the second and third segments, wherein upon linearization of the first plasmid and co-transformation with the second plasmid of bacterial cells, the adenoviral vector and linearized first plasmid recombine to form a recombinant adenoviral vector comprising the desired gene.

In another embodiment of the invention, a bacterial cell is provided for homologous recombination of two DNA molecules containing adenoviral sequences. The first DNA molecule is a linear DNA molecule which comprises a first segment of DNA comprising a desired gene inserted in a restriction enzyme site; a second and a third segment of DNA consisting of adenoviral genomic DNA, each of said second and third segments consisting of at least 500 bp and being sufficient to mediate homologous recombination with an adenoviral vector, wherein the second and third segments flank the first segment. The second DNA molecule is a plasmid which comprises a bacterial origin of replication flanked on each side by DNA segments identical to the second and third segments, whereby the adenoviral vector and the linear DNA molecule can recombine to form a recombinant adenoviral vector comprising the desired gene.

These and other objects of the invention provide the art with new reagents and methods for making recombinant adenoviral vectors containing transgenes for expression in mammalian cells.

BRIEF DESCRIPTION OF THE DRAWINGS

FIG. 3A. DNA from recombinant pAdEasy-GFP+GAL constructs derived from homologous recombination of pAdTrack-CMV-βgal and pAdEasy-1 in BJ5183 cells was purified from minipreps. The DNA was analyzed in supercoiled form by electrophoresis through a 0.8% agarose gel and ethidium bromide staining. Lane 1, pAdEasy-1 control; lane 2, pAdTrack-GFP+GAL control; lanes 3–12, different pAdEasy-GFP+GAL clones. Based on the migration rates, the clones in lanes 3, 4, 6, 8, 9, 11, and 12 were potential valid recombinants. FIG. 3B. Representative digestions with BamHI (lanes 1–3), PacI (lanes 4–6), and SpeI (lanes 7–9). Plasmids pAdTrack-CMV (lanes 1, 4, and 7), pAdEasy-1 (lanes 2, 5, and 8) and a pAdEasy-GFP+GAL recombinant (lanes 3, 6, and 9) are shown. Asterisks indicate the diagnostic fragments obtained with each enzyme.

DETAILED DESCRIPTION OF THE INVENTION

Figure 1:
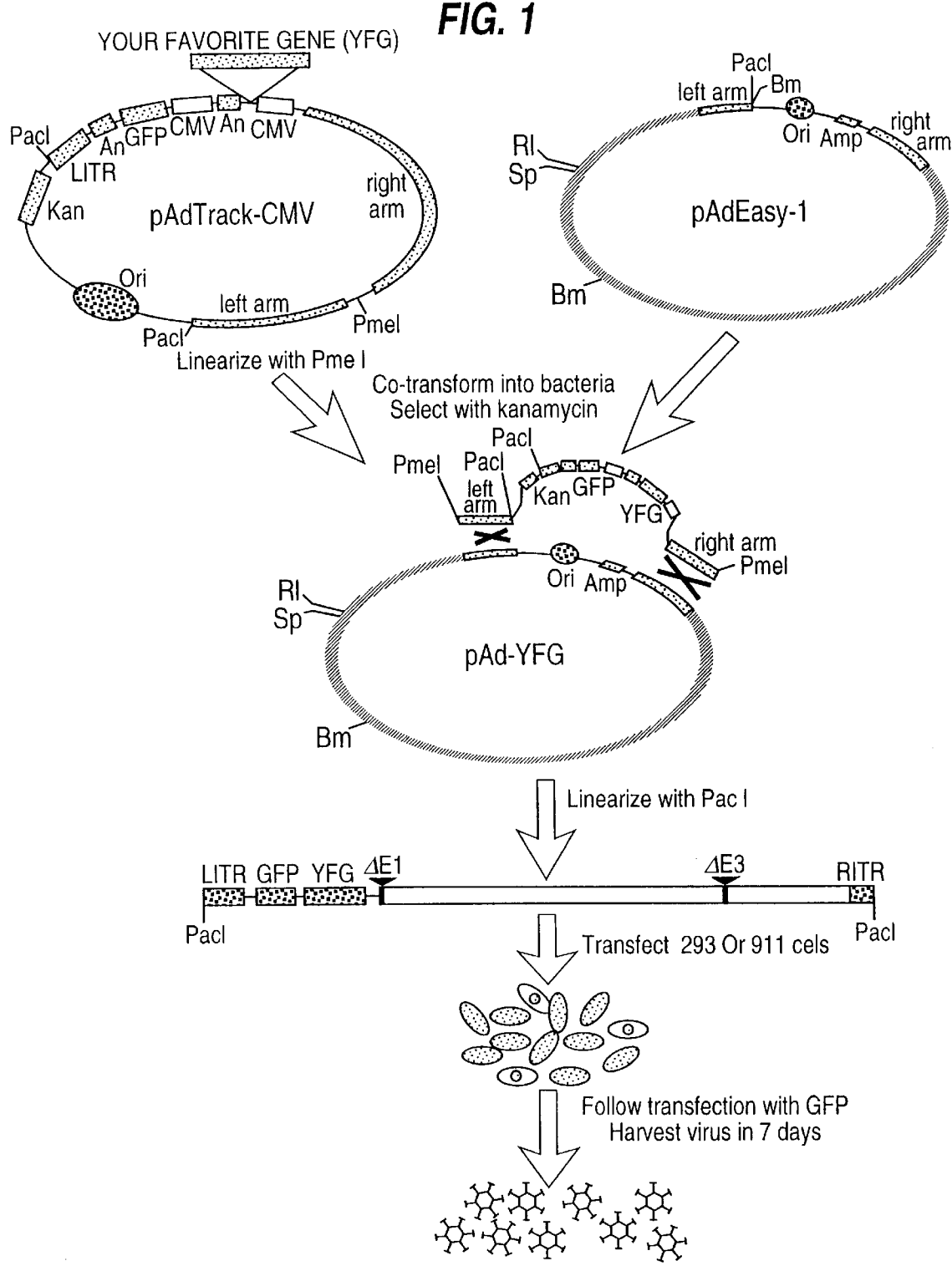
FIG. 1 is a schematic outline of the adenoviral recombination system. The gene of interest is first cloned into a shuttle vector, e.g. pAdTrack-CMV. The resultant plasmid is linearized by digesting with restriction endonuclease Pme I, and subsequently cotransformed into E. coli BJ5183 cells with an adenoviral backbone plasmid, e.g., pAdEasy-1. Recombinants are selected for kanamycin resistance, and recombination confirmed by multiple restriction endonuclease analyses. Finally, the linearized recombinant plasmid is transfected into adenovirus packaging cell lines, e.g. 911 or 293 cells. Recombinant adenoviruses are typically generated within 7 to 12 days. The left arm and right arm represent the regions mediating homologous recombination between the shuttle vector and the adenoviral backbone vector. An: polyadenylation site, Bm: BamHI, RI: EcoRI; LITR: left-hand inverted terminal repeat and packaging signal; RITR: right-hand inverted terminal repeat; Sp: SpeI.

We have discovered methods for generating adenoviral vectors which are more efficient than alternative systems for producing viral recombinants (13–16). According to the present invention, a backbone vector, containing most of the adenoviral genome, is used in supercoiled form, obviating the need for enzymatic manipulation. Recombination between the adenoviral genome and transgenes is performed in E. coli rather than in mammalian cells. No ligation steps are involved in generating the adenoviral recombinants, as the process takes advantage of the highly efficient homologous recombination machinery present in bacteria. The particular vectors described here allow inclusion of up to 10 kb of transgene sequences, and allow multiple transgenes to be produced from the same virus. Some of the new vectors contain a green fluorescent protein (GFP) gene incorporated into the adenoviral backbone, which permits direct observation of the efficiency of transfection and infection, processes which have been difficult to follow with adenoviruses in the past. These characteristics result in a highly efficient viral production system which obviates the need for plaque purification and significantly decreases the time required to generate usable viruses.

The adenoviral vectors generated by the present invention can be used to transfer one or more desired genes into mammalian cells. The desired genes may be wild-type, mutant, or synthetically modified human genes, genomic DNA, cDNA, or chemically synthesized polynucleotides. The desired genes can be derived from any species or may be non-naturally occurring. The desired genes can be inserted at a restriction endonuclease cleavage site as is known in the art, e.g., using a DNA ligase.

A key step in the generation of adenoviral plasmids according to the present invention is the co-transformation of bacteria with precursor DNA molecules: a linear DNA molecule and a supercoiled adenoviral vector. Transformation is the introduction of DNA into a bacterial cell. Transformation can be carried out by a number of techniques known in the art. Such methods include but are not limited to electroporation (exposure of a cell suspension to an electrical field), the use of calcium phosphate solutions, and the use of lipids to package the DNA and fuse with the cell membrane. Co-transformation refers to the introduction of two different species of DNA molecule into the same cell.

The linear DNA molecule for use in co-trasformation in the current invention can be obtained from a circular plasmid DNA molecule by treatment with a restriction endonuclease. The circular plasmid DNA molecule typically contains a bacterial origin of replication and thus is capable of reproducing in bacterial cells. The plasmid may optionally contain several additional segments of DNA. A segment of DNA is a portion of a DNA molecule. The plasmid desirably comprises one or more desired genes. In addition, segments of DNA consisting of adenoviral sequences flank the desired genes to promote homologous recombination with an adenoviral vector.

The adenoviral vector typically contains most of the adenoviral genome and is supercoiled. The adenoviral vector may also contain a bacterial origin of replication. Portions of the wild-type adenoviral genome may be deleted to permit insertion of desired genes and the packaging of recombinant adenoviral vectors containing the desired genes.

A kit according to the invention comprises two plasmids, one of which can be used to generate the the linear DNA molecule discussed above and the other of which is the adenoviral vector. A user of the kit may insert one or more desired genes into the first plasmid using, for example, a restriction endonuclease and a DNA ligase. The kit may also comprise a packaging cell line for producing virus particles from the defective adenoviral vector and/or the recombinant adenoviral vectors produced containing the desired gene. The kit may also comprise bacterial cells which can be used for co-transformation. Preferably the bacterial cells are homologous-recombination proficient and highly competent to receive transforming DNA. Typically, each kit component is separately packaged to avoid premature mixing. Further, all individually packaged components are provided in a box or other container which holds the other components.

Instructions for making a recombinant adenovirus vector according to the methods disclosed herein may also be included in the kit. Reference to instructions may also be provided in the kit, for example to a text or webpage.

The present invention utilizes recombination in bacteria to combine the linear DNA molecule, containing a desired gene, with the adenoviral vector. Recombination is a process in which two DNA molecules become joined. Homologous recombination occurs between two sequences having regions of homology. Bacterial recombination is particularly robust. In order to facilitate recombination between the linear DNA molecule and the adenoviral vector, identical sequences must be present in both. Using standard methods in the art, segments of the adenoviral genome can be put on the linear DNA molecule to create regions of homology.

The segments of adenoviral DNA on the linear DNA molecule are preferably at least 100, 200, 300, 400, 500, 750, or 1000 nucleotide base pairs, such that adequate homology is provided for homologous recombination to occur efficiently. The segments of adenoviral DNA flank the desired gene, i.e., they are on opposite sides of the desired gene sequence; however, the segments need not be contiguous with the desired gene. In the adenoviral vector, the segments may flank the bacterial origin of replication.

When the linear DNA molecule and the supercoiled adenoviral vector recombine in bacterial cells, they form a recombinant adenoviral vector. The recombinant vector can be linearized to enhance efficiency of transfection of mammalian cells. This can be conveniently accomplished through the use of a restriction endonuclease. Preferably the endonuclease cleaves the recombinant adenoviral vector so that its inverted terminal repeat sequences are at the ends of the linearized recombinant vector.

Bacterial cells for use in the present invention preferably are gram negatives. More preferably they are *E. coli*. Desirably they are recombination proficient.

The recombinant adenovirus vector generated as described above may be used to transfect mammalian cells. Techniques for transfection are well known. Available techniques include but are not limited to electroporation, the use of calcium chloride, and packaging of the vector together with lipid for fusion with the cells of interest. Cells may be transfected with the vector either in vitro or in vivo. The design of the recombinant adenoviral vector may place specific constraints on cells to be transfected. If production of viral particles is desired, a special packaging cell must be used that produces the adenoviral gene products which the adenoviral vector lacks. Which packaging cells are employed to replicate the virus will depend on the composition of the adenoviral vector used. The adenoviral vector may have specific portions of the adenoviral genome deleted, in order to make room for the desired gene in the recombinant vector. Suitable deletions which may be used include those of all or part of adenoviral transcription units E1, E3, and E4. The packaging cells preferably stably express the adenoviral proteins coded by the deleted transcription units. Techniques are known in the art for stably transfecting a cell line with whichever adenoviral sequences are required, i.e., by incorporation of the genes into the cell's genome. If virus particle production is not required, then packaging cell lines need not be used. For example, if cells are to express the transgene, production of viral particles need not be achieved. Thus for in vivo gene therapy, the recipient cells need not be able to complement the defective viruses.

Genes encoding a detectable marker may be present in the linear DNA molecule between the two segments of adenoviral DNA. The detectable marker is a protein that can be detected. Preferably, a marker is used which is easy to monitor. More preferably a marker is used which can be detected even when present at very low levels. Use of a detectable marker permits monitoring of the transfection process. In a preferred embodiment the detectable marker is β-galactosidase or green fluorescent protein (GFP). Detection of GFP can be achieved, for example, by fluorescence microscopy of cultured cells.

Genes encoding a selectable product can also be used as linked markers to the desired gene. A selectable product is necessary for growth under a particular set of conditions. Thus it can be used to selectively grow only those cells that have been transformed or transfected. A preferred selectable product is an antibiotic resistance enzyme, such as a neomycin phosphotransferase.

Though several systems for generating recombinant viruses through Cre-mediated or homologous recombination in yeast or bacteria have been described in the literature (13–15,25), the system described here has several advantages in terms of ease and speed. The fact that the adenoviral components of the system can be used in supercoiled form poses advantages in terms of the reproducibility and stability of the derived recombinants. The ability to recover reasonable quantities of homogeneous virusus after primary transfection of packaging cells, without plaque purification, represents a major practical advantage. And the GFP tracer makes it possible to follow all stages of the viral production process in a convenient fashion. In the case of cells which are inefficiently infected by adenoviruses, the GFP tracer additionally makes it possible to isolate expressing cells through fluorescence-activated cell sorting and thereby facilitate several kinds of experiment. Finally, the system described here is efficient enough so that small libraries of transgenes produced in adenoviruses can be envisioned. Viruses with a particular modification of a transgene (produced by degenerate PCR, for example) could be selected in vivo from a pool of viruses on the basis of functional assays, and the sequence of the selected virus determined by sequencing appropriate PCR products.

The above disclosure generally describes the present invention. A more complete understanding can be obtained by reference to the following specific examples which are provided herein for purposes of illustration only, and are not intended to limit the scope of the invention.

EXAMPLE 1

Generation of Adenoviral Recombinants

Figure 2:
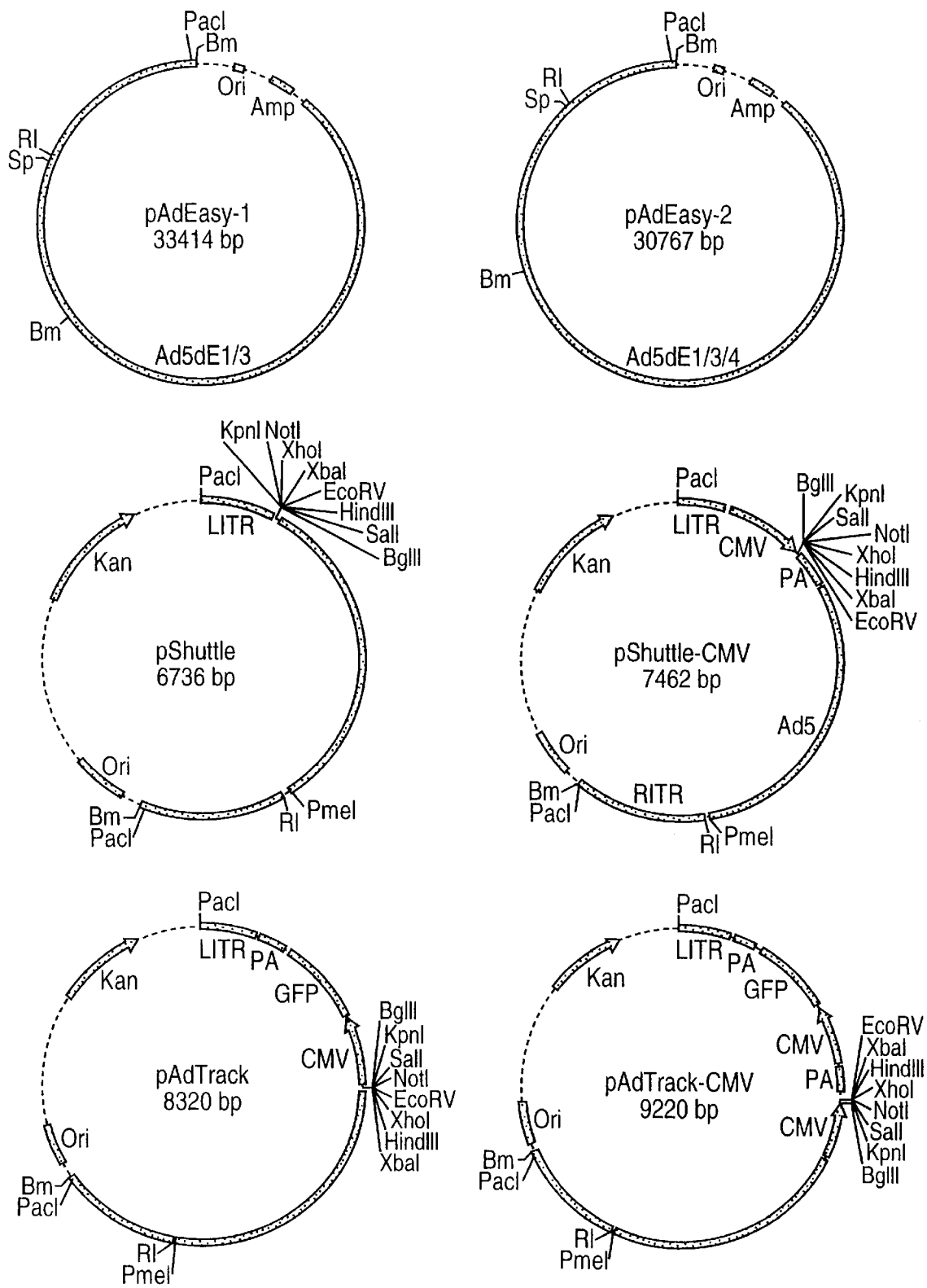
FIG. 2 describes the shuttle vectors and adenoviral plasmids. Abbreviations are defined in the legend to FIG. 1.

The overall strategy involves three steps and is diagrammed in FIG. 1. First, the gene of interest is cloned into a shuttle vector (e.g., pAdTrack-CMV, FIG. 2). Second, the resultant construct is cleaved with a restriction endonuclease to linearize it and then transformed together with a supercoiled adenoviral vector (e.g., pAdEasy-1) into *E. coli* strain BJ5183. Recombinants are selected with kanamycin and screened by restriction endonuclease digestion. Third, the recombinant adenoviral construct is cleaved with PacI to expose its inverted terminal repeats and transfected into a packaging cell line (e.g., 293 or 911 cells) (11,17).

In the past, validation of successful virus production at early stages of the process has been one of the most technically demanding aspects of adenoviral vector production. The process of viral production can be directly and conveniently followed in the packaging cells by visualization of a GFP reporter that is incorporated into the viral backbone. After 7–10 days, viruses are harvested and either used directly for experimentation or amplified by infecting packaging cells.

Important points about this approach include the following: (i) Several different shuttle vectors were constructed. Some, like pAdTrack and pAdTrack-CMV, allow convenient tracing of all steps in viral production through an incorporated GFP reporter. Others, like pShuttle, are used when particularly large transgenes must be expressed. Table 1 lists optimum combinations of shuttle and backbone vectors for various purposes. (ii) The homologous recombination step is mediated by a restriction endonuclease-cleaved vector (like pAdTrack-CMV) and an intact supercoiled adenoviral vector (like pAdEasy-1). The ability to use intact adenoviral plasmids, uncleaved by restriction endonucleases, proved critical for efficiently generating desired recombinants. An additional advantage of using supercoiled adenoviral vectors is that preparation of a single, laboratory-scale batch of the adenoviral vector DNA will yield sufficient material for hundreds of different recombinants. (iii) The selection of recombinants is afforded by kanamycin resistance provided by the shuttle vector. Because the restriction-cleaved shuttle vector yields only a low background of kanamycin-resistant colonies, the homologous recombination system had a high signal-to-noise ratio. (iv) The *E. coli* strain BJ5183 is not recA but is deficient in other enzymes which mediate recombination in bacteria. It was chosen, from among several strains mutated in recA, recBCD, recj, or recF (21,22), because of its higher efficiency of transformation and stable propagation of plasmid DNA in pilot experiments. Once recombination is achieved and verified, the adenoviral recombinant DNA can be simply transferred to a recA, endA strain (such as DH10B) for greater yields of DNA if desired. (Because of its recA status, DH10B cannot be used to generate adenoviral recombinants by homologous recombination). (v) For viruses containing two independent transcription units driven by the same promoter, we found it important to place them in head-to-head, orientation, rather than head-to-tail, in order to avoid undesired recombination events in bacteria. (vi) The packaging cell lines (293, 911, or 911E4) are each highly transfectable by lipid-DNA complexes. The 293 and 911 cells constitutively express the E1 gene products required for propagation of all recombinant adenoviruses, while the 911E4 cells express the E1 and E4 gene products required for pAdEasy-2-derived constructs.

Cell Culture, Medium and Reagents. 293 cells (11) were purchased from Microbix Biosystems Inc. (Toronto, Canada), and 911 cells (17) were kindly provided by Dr. Alex J. Van der Eb of the University of Leiden. These lines were maintained in Growth Medium (Dulbecco's Modified Eagle Medium, Life Technologies, Inc., Gaithersburg, Md., supplemented with 10% fetal bovine serum [FBS, Hyclone, Logan, UT], 100 units/ml penicillin, and 100 mg/ml streptomycin) at 37° C. in 5% $CO_2$.

Preparation of Competent Cells and Plasmid DNAs. To prepare electrocompetent BJ5183 bacteria (18), the cells were grown to an $OD_{550}$ of 0.8, then collected and washed twice with ice-cold 10% glycerol. Twenty ml aliquots of the electrocompetent BJ5183 cells were kept at −80° C. Electrocompetent DH10B cells were purchased from Life Technologies, Inc. To verify homologous recombination in bacteria, miniprep plasmid DNA was prepared by a standard alkaline lysis procedure. All other plasmids used in this study were prepared by CsCl banding. Yields were 200 to 600 μg per 100 ml of Terrific Broth culture (Life Technologies) for plasmids larger than 30 kb (pAdEasy derivatives), and 400 to 1000 mg for plasmids smaller than 15 kb (shuttle plasmid derivatives).

Establishment of an Adenoviral E4-Expressing Cell Line. A plasmid that constitutively expresses tet repressor in the same transcription unit as a geneticin-resistance marker was transfected into 911 cells. Following growth in geneticin (0.4 mg/ml, Life Technologies), a clone stably expressing the tet repressor, 911tet, was chosen for further manipulation. A second vector that expressed adenoviral E4 under the control of tet responsive promoter was constructed by cloning a fragment containing adenoviral nt 35,468–32,828 into the pBI vector (Clontech), resulting in pBI-E4. The pBI-E4 plasmid was co-transfected with linearized pCEP4 (Invitrogen, Carlsbad, Calif.) into 911 tet cells. Stable clones were generated through selection in 0.4 mg/ml geneticin, 0.1 mg/ml hygromycin B (CALBIOCHEM), and 100 ng/ml doxycyclin (Sigma). A single clone, called 911-E4, was chosen for viral production based on its tight regulation of E4 protein expression. Expression of adenoviral E4 after removal of doxycyclin was confirmed by immunohistochemical analysis using a monoclonal antibody against E4ORF6, kindly provided by P. Hearing (SUNY, Stoney Brook) (19).

Construction of Vectors for Homologous Recombination in Bacteria. The adenoviral plasmids (pAdEasy-1 and pAdEasy-2) and the shuttle vectors (pShuttle, pShuttle-CMV, pAdTrack, and pAdTrack-CMV) were constructed through multiple rounds of subcloning of PCR products or of restriction endonuclease fragments. All PCR-derived fragments were sequenced to confirm their predicted composition.

1. Adenoviral backbone vectors.

a. The pAdEasy-1 adenoviral plasmid contains all Ad5 sequences except nt 1–3,533 (including the E1 genes) and nt 28,130–30,820 (including E3).

b. The pAdEasy-2 vector is identical to pAdEasy-1 except that it contains an additional deletion of Ad5 nt 32,816–35,462 (containing E4).

2. Shuttle vectors.

a. Vector pShuttle is used for expression of transgenes when no GFP tracer is desired. It contains a polylinker for insertion of exogenous transgenes. This site is surrounded by adenoviral sequences ("arms") that allow homologous recombination with pAdEasy-1. The left arm contains Ad5 nt 34,931–35,935, which mediates homologous recombination with pAdEasy vectors in *E. coli*, plus inverted terminal repeat (ITR) and packaging signal sequences (nucleotides 1 to 480 of Ad5) required for viral production in mammalian cells. The right arm contains Ad5 nt 3,534–5,790, which mediate homologous recombination with pAdEasy vectors. Artificially created PacI sites surround both arms. The pShuttle plasmid also contains a kanamycin resistance gene from pZero 2.1 (Invitrogen) and the origin of replication from pBR322 (Life Technologies). We have found, as have others, that the relatively low copy number of plasmids generated with this origin is essential for the stability of large constructs in *E. coli*.

b. The pShuttle-CMV vector is identical to pShuttle except for the addition of a CMV promoter and polyadenylation site (both from pEGFP-C1, Clontech). A polylinker is present between the CMV promoter and polyadenylation site.

c. The pAdTrack vector is used for production of GFP-trackable viruses containing transgenes under the control of a chosen promoter. It was constructed by subcloning the gene encoding Enhanced GFP from pEGFP-C1 into pShuttle.

d. The pAdTrack-CMV vector is identical to pAdTrack except for the addition of a CMV promoter and polyadenylation site (as in pShuttle-CMV).

3. Vectors encoding both β-galactosidase and GFP. To test various aspects of these systems, two vectors (pGFP+ GAL-1 and -2) containing β-galactosidase (β-gal) and GFP genes were constructed. Each contained the β-gal gene from pUT651 (Cayla, Toulouse, France). The only difference between pGFP+GAL-1 and pGFP+GAL-2 the two vectors was the presence in GFP+GAL-2 of a "stuffer" fragment from human genomic DNA. pGFP+GAL-2 thereby contained the maximum amount of foreign sequences (~10 kb) possible to be included in the adenovirus systems described here. Both pGFP+GAL-1 and pGFP+GAL-2 contained two independent CMV-driven transcription units (one for GFP and one for β-gal).

Generation of Recombinant Adenoviral Plasmids by Homologous Recombination in *E. coli*. High competence of bacterial cells is desired to achieve efficient recombination. Typically, 0.5 to 1.0 μg of a shuttle vector plasmid (about one-fifth of a miniprep) was linearized with PmeI, purified by phenol/chloroform extraction and ethanol precipitation, and mixed with 0.1 mg of supercoiled pAdEasy-1 or pAdEasy-2 in a total volume of 6.0 μl. Twenty μl of electrocompetent *E. coli* BJ5183 cells were added and electroporation was performed in 2.0 mm cuvettes at 2,500 V, 200 Ohms, and 25 μFD in a Bio-Rad Gene Pulser electroporator. The cells were immediately placed in 500 μl of L-Broth (Life Technologies, Inc.) and grown at 37° C. for 20 min. 125 μl of the cell suspension was then inoculated onto each of four 10 cm Petri dishes containing L-agar plus 50 μg/ml kanamycin. After 16–20 hr. growth at 37° C., 10–25 colonies per dish were generally obtained. The smaller colonies (which usually represented the recombinants) were picked and grown in 2 ml L-Broth containing 50 μg/ml kanamycin. Clones were first screened by analyzing their supercoiled sizes on agarose gels, comparing them to pAdEasy-1 or pAdEasy-2 controls. Those clones which had inserts were further tested by restriction endonuclease digestions, generally PacI, SpeI, and BamHI. (Recombinations sometimes occurred between the plasmid Ori sequences shared between the shuttle and pAdEasy vectors; such recombinants were as useful as those generated by homologous recombination of the "left arm" sequences, but resulted in slightly different restriction patterns; see map in FIG. 1). Once confirmed, supercoiled plasmid DNA was transformed into DH10B cells for large scale amplification by electroporation. In such cases, 1.0 μl of plasmid DNA (100 ng) in 15 μl water was mixed with 5.0 μl electrocompetent DH10B cells in a total volume of 20.0 μl and electroporation was performed as described above.

Production of Adenoviruses in Mammalian Cells. Approximately $1.5 \times 10^6$ cells (911, 293, or 911E4) were plated in 25 cm² flasks 24 hours prior to transfection, by which time they reached 50–70% confluency. Cells were washed once with 3 ml OptiMEM (Life Technologies), then 2.5 ml of OptiMEM was added to each flask and the flasks returned to the $CO_2$ incubator for 15–30 minutes prior to transfection. Four μg of recombinant adenoviral vector DNA, digested with PacI and ethanol-precipitated, wasere used for transfection of each 25 cm² flask. A transfection mix was prepared by adding 4 μg of linearized plasmid DNA and 20 μl LipofectAmine (Life Technologies) to 500 μl of OptiMEM (Life Technologies) according to the manufacturer's instructions. After incubation at room temperature for 15 to 30 minutes, the transfection mix was added to the cells. After 4 to 6 hours at 37°, the media containing the transfection mix was removed, and 6 ml of Growth Medium added. For transfections of 911E4 cells, doxycyclin was removed from the Growth Media ~24 hours after transfection. Transfected cells were monitored for GFP expression and collected 7 to 10 days after transfection by scraping cells off flasks and pelleting them along with any floating cells in the culture. All but 3 ml of the supernatant was removed. Following three cycles of freezing in a methanol/dry ice bath and rapid thawing at 37°, one ml of viral lysate was used to infect $3-5 \times 10^6$ cells in a 25 cm² flask. The efficiency of such infections could be conveniently followed with GFP. Three to four days later, viruses were harvested as described above. At this point, viral titers were often high enough to use for gene transfer experiments in cultured cells. To generate higher titer viral stocks, packaging cells were infected at an MOI (multiplicity of infection) of 0.1 to 1 and grown for 3 to 4 days, at which time viruses were harvested as described above. This process was repeated one to three times, with a final round employing a total of $5 \times 10^8$ packaging cells in fifteen 75 cm² flasks and an MOI of 1–5. After 3–5 days, 50% lysis was observed, and the resultant viruses were purified by CsCl banding; final yields were generally $10^{11}$ to $10^{12}$ pfu. Restriction endonuclease digestions confirmed the expected structures of the viruses produced in this way. Procedures for CsCl banding and viral plaquing are described in ref 20.

EXAMPLE 2

Generation of a Recombinant Adenovirus Containing β-gal

Figure 3A:
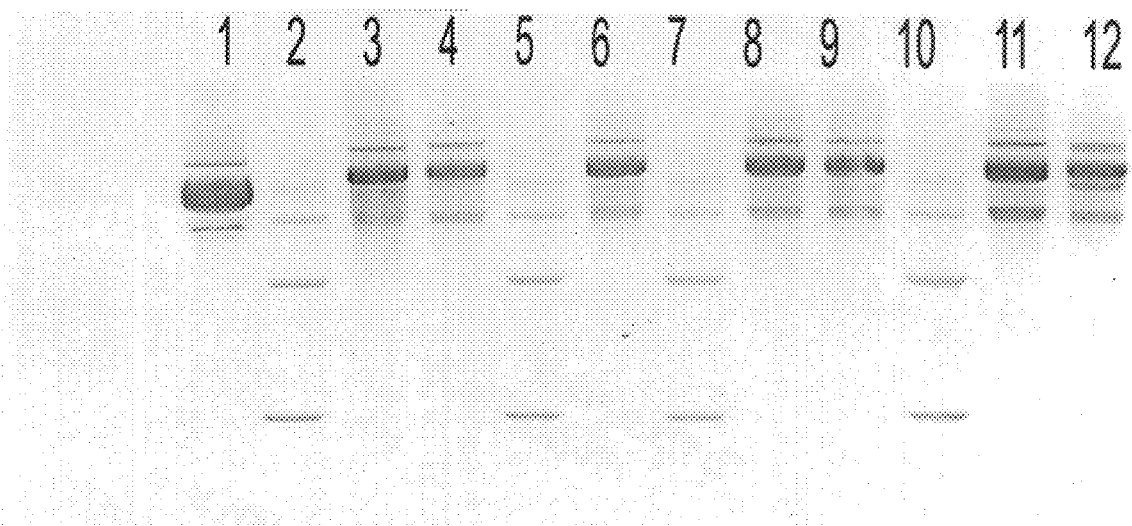
FIGS. 3A and 3B describe the generation of stable recombinants in bacterial cells.
Figure 3B:
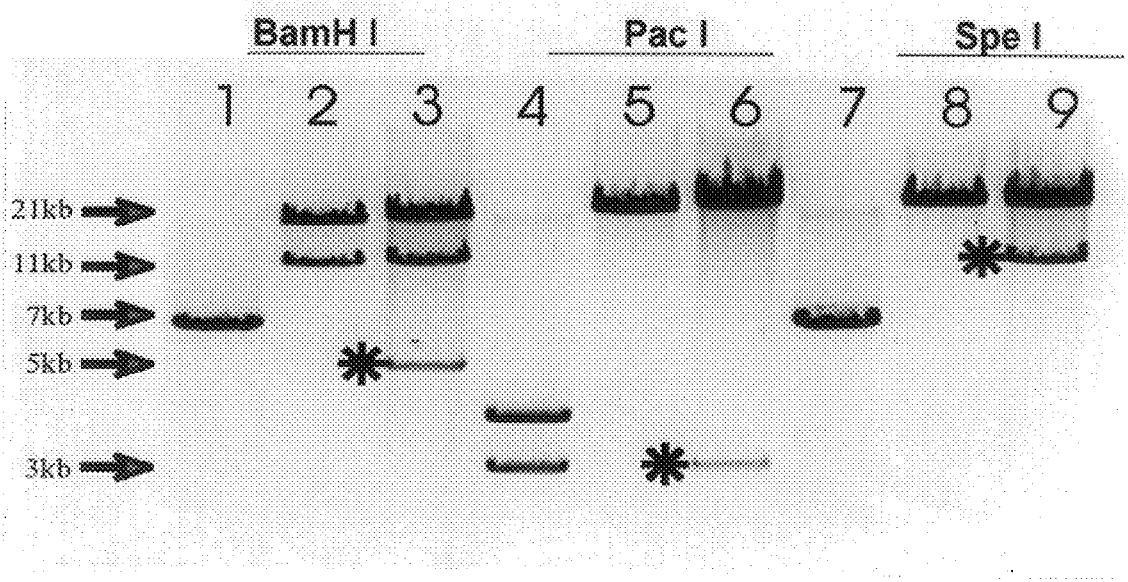

The results obtained while generating a virus encoding β-gal provide a representative example of the yields and other practical considerations. A β-gal cDNA was placed in the polylinker of pAdTrack-CMV to generate the shuttle vector pGFP+GAL. To make pAdEasy-GFP+GAL, one μg of linearized pGFP+GAL was co-transformed with 0.1 μg of supercoiled circular pAdEasy-1 into *E. coli* BJ5183 cells (see vector diagrams in FIG. 2). The transformation yielded about 100 kanamycin-resistant clones, of which approximately two-thirds contained recombinants based on the sizes of undigested miniprep plasmid DNA (FIG. 3A). Candidate clones were digested with several restriction endonucleases to verify proper recombination. As shown in FIG. 3B, the expected restriction fragments were generated in each case. For example, with BamHI, a 5.1 kb fragment containing the GFP gene was produced from pAdEasy-GFP+GAL (lane 3) in addition to the 11.7 and 21.7 kb fragments generated from pAdEasy-1 sequences (lane 2). When digested with PacI, a 3.0 kb fragment was produced (FIG. 3B, lane 6).

Plasmids could be produced directly from *E. coli* BJ5183 cells, but the yields were relatively low (<0.5 μg from 2 ml culture). Therefore, miniprep DNA from *E. coli* BJ5183 cells was used to transform DH10B cells, a recA strain in which high quality and high yields of plasmid DNA can be obtained more easily. Yields of supercoiled pAdEasy-derived vectors averaged 2–5 μg per ml from DH10B cells.

EXAMPLE 3

Figure 4:
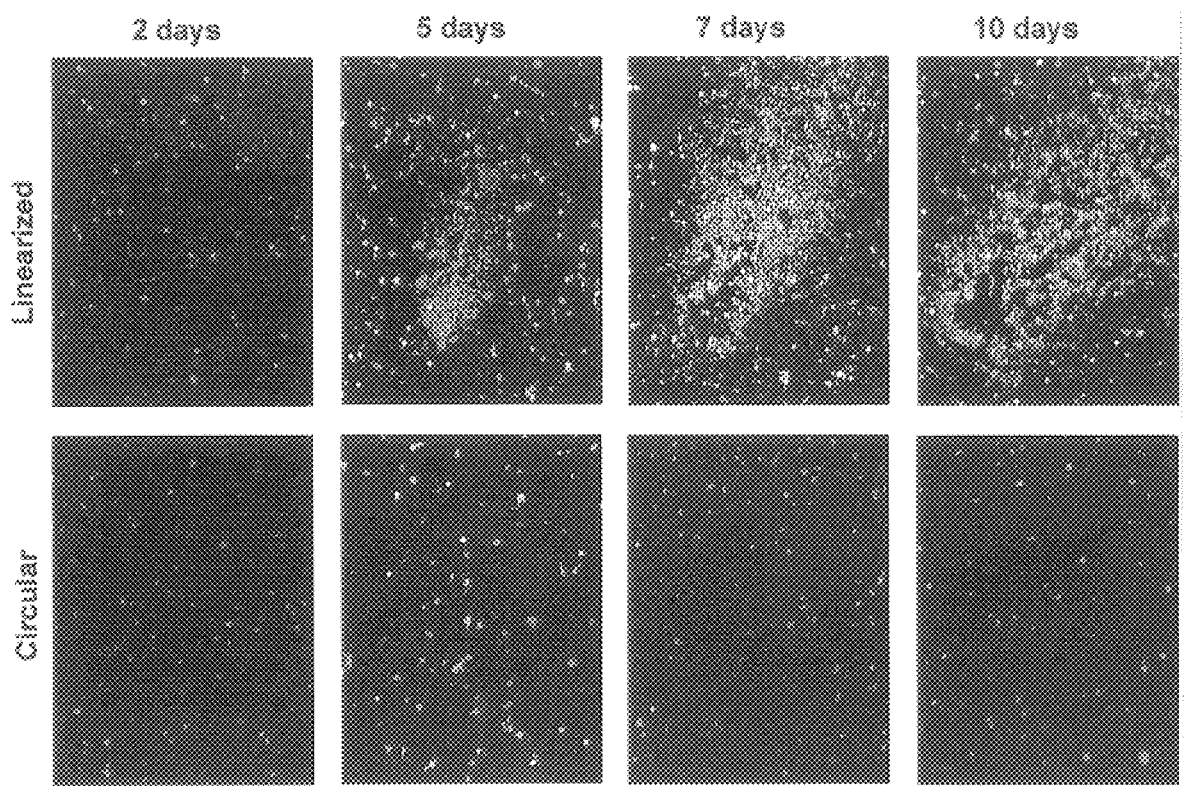
FIG. 4 shows adenoviral-producing foci following transfection of 293 cells monitored by GFP expression. PacI-digested pAdEasy-GFP–GAL was transfected into 293 cells and GFP expression was visualized by florescence microscopy at the indicated times thereafter. Comet-like adenovirus-producing foci became apparent at 4–5 days. No such foci were observed in the cells transfected with circular (i.e., not PacI-digested) pAdEasy-GFP–Gal.

Transfection of Cells with Recombinant Adenovirus and Expression of a Reporter Gene To produce viruses, 4 μg of pAdEasy-GFP+GAL was digested with Pac I to liberate linear adenoviral genomes, then transfected into 293 cells. It was critical to linearize the vectors at the Pac I sites, as transfection of circular plasmids yielded no viruses, consistent with previous results (14, 23, 24). To assess how soon the packaged viral particles could be observed, transfected cells were monitored by GFP expression. As shown in FIG. 4, GFP expression was visible 24 hr after transfection in 20–30% of the cells, representing the fraction of the population that was transfected. In cells transfected with non-linearized pAdEasy-GFP+GAL, this expression slowly faded over one week. In cells transfected with linearized pAdEasy-GFP+GAL, however, this expression never faded, and comet-like foci, visualized with GFP fluorescence but invisible by phase contrast microscopy, began to appear at four to five days after transfection (FIG. 4). Cells in the center of foci were often lysed a week after transfection, though the foci were still very difficult to see without the aid of GFP fluorescence. In cells tranfected with non-linearized pAdEasy-GFP+GAL, GFP expression was initially indistinguishable from that following transfection with the linearized vector. This expression slowly faded over one week, and comet-like foci never appeared (FIG. 4). Interestingly, only 10–50 comet-like plaques were observed per 25 cm$^2$ flask, while >10$^5$ cells expressed GFP following transfection. This was surprising in view of the fact that every 293 cell should theoretically have the capacity to produce virus from the transfected vector. Evidently, degradation of the exogenous DNA or other factors which limit the efficiency of viral production drastically decrease the number of cells which produce virus. These results may explain the difficulties of achieving efficient viral production following homologous recombination (rather than direct transfection) in mammalian cells.

Figure 5:
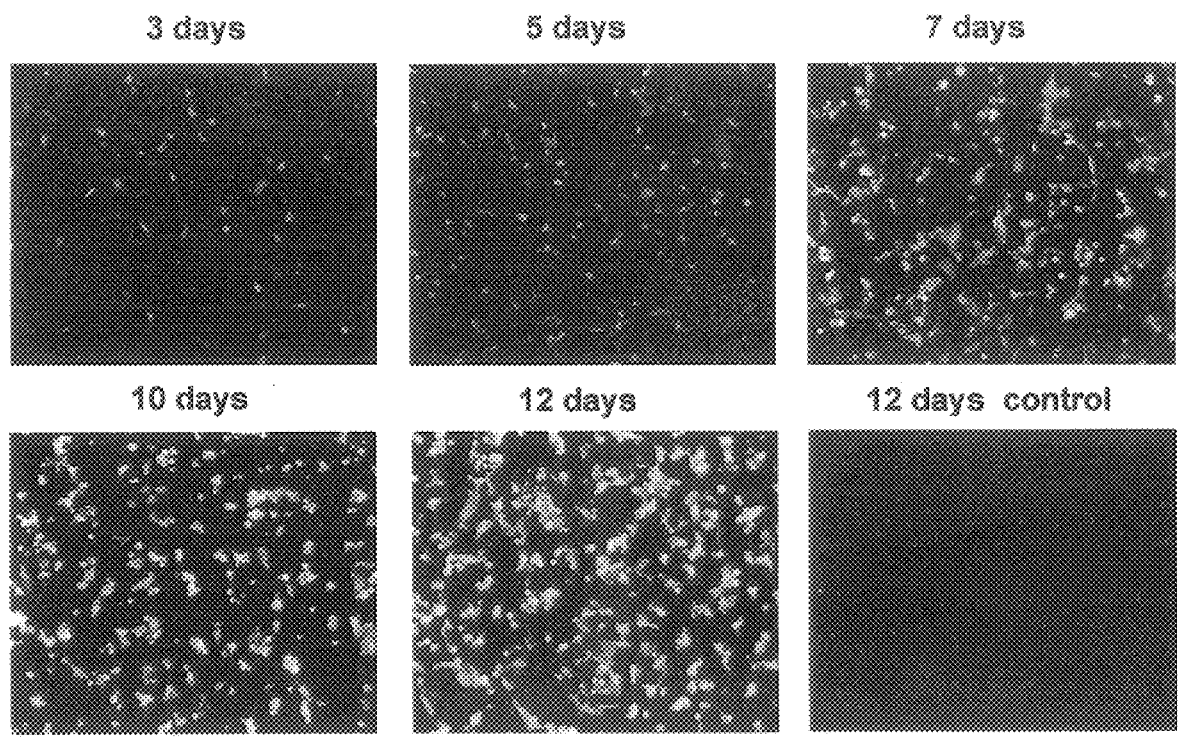
FIG. 5 demonstrates how adenoviral titre can be monitored by GFP expression. Linearized pAdEasy-GFP+GAL was transfected into 293 cells as described in FIG. 4 and cells were harvested at the indicated times after transfection. Three percent of a freeze/thaw lysate of these cells was used to infect 293 cells, and fluorescence microscopy of the infected cells was performed 24 hours later. No viruses were generated in 12 days after the transfection of circular (i.e., not cleaved with PacI) pAdEasy-GFP+GAL (labeled "control").

As another way to assess viral production following transfection of 293 cells, cells were collected and lysed at various times after transfection and the lysates assessed for viral production through transfer of GFP or β-gal expression. In each case, 2% of the viruses harvested from a single transfection were used to infect approximately 10$^5$ recipient 293 cells. As shown in FIG. 5, significant amounts of virus were present as early as three days following transfection, concordant with the appearance of first observable viral foci (FIG. 4). Viral titers increased substantially over the next week (FIG. 5). Importantly, β-gal expression perfectly paralleled GFP expression, as assessed in three ways. First, the titer of virus, assessed by X-gal staining of infected cells, was identical to that determined from GFP expression of the same cultures prior to X-gal staining. Second, when GFP expressing cells were marked prior to staining with X-gal, every cell that expressed GFP was also found to express β-gal and vice versa. And third, standard plaque assays demonstrated that virtually all (>95%) plaques expressed both GFP and β-gal (data not shown). This homogeneity among the plaques was important for another reason: it obviated the need, in general, to plaque-purify viruses. Such plaque purification represents one of the most time-consuming steps in classical adenovirus vector production.

The titer of the homogeneous viruses produced 7–12 days after transfection of 911 or 293 cells ranged from 10$^6$ to 10$^8$ expression forming units (efu)/ml on 293 cells. In the experiment shown in FIG. 5, the titer was 1 efu/ml. The titer generally was proportional to the efficiency of transfection of the packaging line. Titers determined by plaque assays (expressed in standard plaque forming units) were equivalent. These viruses could be used to achieve gene expression in a variety of cell lines of human, mouse, and hamster origin. The titer levels on these additional lines were similar to that achieved with adenoviruses made by classical methods, and differences in expression likely reflected differences in adenovirus receptors and processing among the various lines. In the human colorectal cancer cell line HCT116, titer was 20- to 200-fold lower than that achieved in 293 or 911 cells.

EXAMPLE 4

Expression of Large or Multiple Transgenes

Similar experiments were carried out with an adenovirus containing both GFP and β-gal genes expression units plus a "stuffer." The total foreign sequences contained in this virus were 10.1 kb, necessitating use of the pAd-Easy-2 adenoviral vector and a packaging line expressing adenoviral E4 plus E1 genes. In general, viral production using the pAdEasy-2-based system was somewhat slower (10–14 days to produce viral titers equivalent to those produced in 7–10 days in 911 or 293 cells) and the final viral titers about 10-fold lower than with pAdEasy-1 based systems. Therefore, pAdEasy-2 and 911-E4 cells were used only to produce viruses containing transgenes too large to produce with pAdEasy-1 (Table 1). In general, 911 cells are the preferred producers for pAdEasy-1-derived viruses, though 293-derived cells also produced acceptable results (17).

TABLE 1

Selection of Vector Systems

| Shuttle plasmid | Adenoviral backbone | Packaging cells | Maximum insert size | GFP Tracer | Use |
|---|---|---|---|---|---|
| pAdTrack-CMV | pAdEasy-1 | 293 or 911 | 5.0 kb | Yes | Standard for expression of transgene under CMV promoter |
| pAdTrack-CMV | pAdEasy-2 | 911E4 | 7.7 kb | Yes | Used only for expression of large genes under CMV promoter |
| pAdTrack | pAdEasy-1 | 293 or 911 | 5.9 kb | Yes | Expression of transgene(s) under a chosen (non-CMV) promotor |
| pAdTrack | pAdEasy-2 | 911E4 | 8.6 kb | Yes | Used only for expression of a large gene(s) under a chosen (non-CMV) promotor |
| pShuttle-CMV | pAdEasy-1 | 293 or 911 | 6.6 kb | No | Standard for expression of transgene under CMV promoter |
| pShuttle-CMV | pAdEasy-2 | 911E4 | 9.3 kb | No | Used only for expression of large gene under CMV promoter |
| pShuttle | pAdEasy-1 | 293 or 911 | 7.5 kb | No | Expression of transgene(s) under a chosen (non-CMV) promoter |
| pShuttle | pAdEasy-2 | 911E4 | 10.2 kb | No | Used only for expression of a large gene(s) under a chosen (non-CMV) promoter |

REFERENCES

1. Miller, A. D. (1992) Nature 357, 455–460.
2. Morgan, R. A. & Anderson, F. A. (1993) Annu. Rev. Biochem. 62, 191–217.
3. Graham, F. L. & Prevec, L. (1991) Meth. Mol. Biol. 7, 109–128.
4. Berkner, K. L. (1988) BioTechniques 6, 616–629.

5. Shenk, T. (1996) in Fields Virology, eds Fields, B. N., Knipe, D. M., Howley, P. M. et al (Lippincott-Raven, Philadelphia), pp. 2111–2148.
6. Horwitz, M. S. (1996) in Fields Virology, eds Fields, B. N., Knipe, D. M., Howley, P. M. et al (Lippincott-Raven, Philadelphia), pp. 2149–2171.
7. Ballay, A., Leverero, M., Buendia, M. A., et al (1985) EMBO J 4, 3861–3865.
8. Rosenfeld, M. A., Siegfried, W., Yoshimura, K., et al (1990) Science 252, 431–434.
9. Mittal, S. K., McDermott, M. R., Johnson, D. C., et al (1993) Virus Res. 28, 67–90.
10. Stratford-Perricaudet, L. D., Makeh, I., Perricaudet, M., et al (1992) J. Clin. Invest. 90, 626–630.
11. Graham, F. L., Smiley, J., Russel, W. C. & Nairn, R. (1977) J. Gen. Virol. 36, 59–72.
12. Becker, T. C., Noel, R. J., Coats, W. S., Gomez-Foix, A. M., Alam, T., Gerard, R. D. & Newgard, C. B. (1994) Meth. Cell Biol. 43, 161–189.
13. Ketner, G., Spencer, F., Tugendreich, Connelly, C. & Hieter, P. (1994) Proc. Natl. Acad. Sci. U.S.A. 91, 6186–6190.
14. Chartier, C., Degryse, M., Gantzer, M., Dieterie, A., Pavirani, A. & Mehtali, M. (1996) J. Virol. 70, 4805–4810.
15. Crouzet, J., Naudin, L., Orsini, C., Vigne, E., Ferrero, L., Roux, A. L., Benoit, P., Latta, M., Torrent, C., Denefle, P., Mayaux, J. F., Perricaudet, M. & Yeh, P. (1997) Proc. Natl. Acad. Sci. U.S.A. 94, 1414–1419.
16. Prasher, D., Eckenrode, V., Ward, W., Prendergast, F., and Cormier, M. (1992) Gene 111, 229–233.
17. Fallaux, F. J., Kranenberg, O., Creamer, S. J., Houweling, A., van Ormondt, H., Hoeben, R. C. & van der Eb, A. J. (1996) Human Gene Ther. 7, 215–222.
Hanahan, D. (1983) J. Mol. Biol. 166, 557–580.
Obert, S., O Æ Connor, R. J., Schmid, S., & Hearing, P. (1994) Mol. Cell. Biol. 14, 1333–1346.
Becker, T. C., Noel, R. J., Coats, W. S., Gomez-Foix, A. M., Alam, T., Gerard, R. D., & Newgard, C. B. (1994) Methods Cell Biol. 43, 161–189.
21. West, S. (1994) Cell 76, 9–15.
22. Camerini-Otero, R. D. & Hsieh, P. (1995) Annu. Rev. Genet. 29, 509–552.
23. Berkner, K. L. & Sharp, P. A. (1983) Nucleic Acid Res. 11, 6003–6020.
24. Hanahan, D. & Gluzman, Y. (1984) Mol. Cell. Biol. 4, 302–309.
25. Hardy, S., Kitamura, M., Harris-Stansil, T., Dai, Y. & Phipps, M. L. (1997) J. Virol. 71, 1842–1849.

We claim:

1. A method for generating a recombinant adenoviral vector comprising a desired gene, comprising the steps of:
co-transforming *Escherichia coli* bacteria with:
(a) a linear DNA molecule; and
(b) a supercoiled adenoviral vector;
wherein the linear DNA molecule comprises a first segment of DNA comprising one or more desired genes and a second and a third segment of adenoviral genomic DNA, each of said second and third segments consisting of at least 500 bp and being sufficient to mediate homologous recombination with the supercoiled adenoviral vector, wherein the second and third segments flank the first segment, wherein the supercoiled adenoviral vector comprises a bacterial origin of replication flanked on each side by segments of DNA identical to the second and third segments, whereby subsequent to the step of co-transforming, the supercoiled adenoviral vector and linear DNA molecule recombine to form a recombinant adenoviral vector comprising the desired gene.

2. The method of claim 1 wherein the adenoviral vector comprises a deletion of adenovirus transcription unit E1.
3. The method of claim 1 wherein the adenoviral vector comprises a deletion of adenovirus transcription units E1 and E3.
4. The method of claim 1 wherein the adenoviral vector comprises a deletion of adenovirus transcription units E1 and E4.
5. The method of claim 1 wherein the adenoviral vector comprises a deletion of adenovirus transcription units E1, E3, and E4.
6. The method of claim 1 wherein the first segment comprises an inverted terminal repeat of an adenoviral genome.
7. The method of claim 1 wherein the first segment of DNA comprises a marker gene which encodes a detectable marker protein.
8. The method of claim 1 wherein the first segment of DNA comprises a gene encoding a selectable product.
9. A method of generating recombinant adenoviral particles, comprising the steps of:
co-transforming *Escherichia coli* bacteria with:
(a) a linear DNA molecule; and
(b) a supercoiled adenoviral vector;
wherein the linear DNA molecule comprises a first segment of DNA comprising one or more desired genes and a second and a third segment of adenoviral genomic DNA, each of said second and third segments consisting of at least 500 bp and being sufficient to mediate homologous recombination with the supercoiled adenoviral vector, wherein the second and third segments flank the first segment, wherein the supercoiled adenoviral vector comprises a bacterial origin of replication flanked on each side by segments of DNA identical to the second and third segments, whereby subsequent to the step of co-transforming, the supercoiled adenoviral vector and linear DNA molecule recombine to form a recombinant adenoviral vector comprising the desired gene;
linearizing the recombinant adenoviral vector comprising the desired gene to form a linear DNA molecule comprising termini which comprise adenoviral terminal repeats; and
transfecting mammalian cells with the linearized vector, whereby the mammalian cells produce recombinant adenoviral particles comprising the recombinant adenoviral vector which comprises the desired gene.

10. The method of claim 9 wherein the adenoviral vector comprises a deletion of adenovirus transcription unit E1 and the mammalian cells stably express E1.
11. The method of claim 9 wherein the adenoviral vector comprises a deletion of adenovirus transcription units E1 and E3 and the mammalian cells stably express E1.
12. The method of claim 9 wherein the adenoviral vector comprises a deletion of adenovirus transcription units E1 and E4 and the mammalian cells stably express E1 and E4.
13. The method of claim 9 wherein the adenoviral vector comprises a deletion of adenovirus transcription units E1, E3, and E4, and the mammalian cells stably express E1 and E4.
14. The method of claim 9 wherein the step of linearizing is performed using a restriction enzyme.
15. The method of claim 9 wherein the step of linearizing is performed using restriction enzyme PacI.
16. A method of expressing a desired gene in mammalian cells comprising the steps of:
co-transforming *Escherichia coli* bacteria with:
(a) a linear DNA molecule; and (b) a supercoiled adenoviral vector;
wherein the linear DNA molecule comprises a first segment of DNA comprising one or more desired genes and a second and a third segment of adenoviral genomic DNA, each of said second and third segments consisting of at least 500 bp and being sufficient to mediate homologous recombination with the supercoiled adenoviral vector, wherein the second and third segments flank the first segment, wherein the supercoiled adenoviral vector comprises a bacterial origin of replication flanked on each side by segments of DNA identical to the second and third segments, whereby subsequent to the step of co-transforming, the supercoiled adenoviral vector and linear DNA molecule recombine to form a recombinant adenoviral vector comprising the desired gene;

linearizing the recombinant adenoviral vector to form a linear DNA molecule comprising termini which comprise adenoviral terminal repeats; and transfecting mammalian cells with the linearized vector, whereby the mammalian cells express the desired gene.

17. The method of claim 16 wherein the adenoviral vector comprises a deletion of adenovirus transcription unit E1 and the mammalian cells stably express E1.

18. The method of claim 16 wherein the adenoviral vector comprises a deletion of adenovirus transcription units E1 and E3 and the mammalian cells stably express E1.

19. The method of claim 16 wherein the adenoviral vector comprises a deletion of adenovirus transcription units E1 and E4 and the mammalian cells stably express E1 and E4.

20. The method of claim 16 wherein the adenoviral vector comprises a deletion of adenovirus transcription units E1, E3, and E4, and the mammalian cells stably express E1 and E4.

21. The method of claim 16 wherein the step of linearizing is performed using a restriction enzyme.

22. The method of claim 16 wherein the step of linearizing is performed using restriction enzyme PacI.

23. The method of claim 7 wherein the detectable marker is green fluorescent protein.

24. A kit comprising two plasmids:
wherein the first plasmid comprises:
a bacterial origin of replication;
a first segment of DNA comprising a restriction enzyme site for insertion of a desired gene; and
a second and a third segment of DNA consisting of adenoviral genomic DNA, each of said second and third segments consisting of at least 500 bp and being sufficient to mediate homologous recombination with an adenoviral vector, wherein the second and third segments flank the first segment;

wherein the second plasmid is an adenoviral vector which comprises:
a bacterial origin of replication flanked on each side by DNA segments identical to the second and third segments;
wherein upon linearization of the first plasmid and co-transformation with the second plasmid of *Escherichia coli* bacterial cells, the second plasmid and the linearized first plasmid recombine to form a recombinant adenoviral vector comprising the desired gene.

25. The kit of claim 24 wherein the first segment of DNA further comprises a gene encoding a detectable marker.

26. The kit of claim 24 wherein the first segment of DNA further comprises a gene encoding green fluorescent protein.

27. The kit of claim 24 wherein the first segment of DNA further comprises an inverted terminal repeat of adenovirus.

28. An *Escherichia coli* bacterial cell comprising a plasmid and a linear DNA molecule, wherein the linear DNA molecule comprises:
a first segment of DNA comprising a desired gene inserted in a restriction enzyme site;
a second and a third segment of DNA consisting of adenoviral genomic DNA, each of said second and third segments consisting of at least 500 bp and being sufficient to mediate homologous recombination with an adenoviral vector, wherein the second and third segments flank the first segment;

wherein the plasmid is an adenoviral vector which comprises:
a bacterial origin of replication flanked on each side by DNA segments identical to the second and third segments, whereby the plasmid and the linear DNA molecule can recombine to form a recombinant adenoviral vector comprising the desired gene.

29. The bacterial cell of claim 28 wherein the first segment of DNA further comprises a gene encoding a detectable marker.

30. The bacterial cell of claim 28 wherein the first segment of DNA further comprises a gene encoding green fluorescent protein.

31. The bacterial cell of claim 28 wherein the first segment of DNA further comprises an inverted terminal repeat of adenovirus.

32. The bacterial cell of claim 28 wherein the first segment of DNA comprises a bacterial origin of replication.

* * * * *